United States Patent [19]

van den Bosch

[11] Patent Number: 5,648,081
[45] Date of Patent: Jul. 15, 1997

[54] ACTINOBACILLUS PLEUROPNEUMONIAE SUBUNIT VACCINE

[75] Inventor: Johannes Franciscus van den Bosch, Boxmeer, Netherlands

[73] Assignee: Akzo Nobel N.V., Arnhem, Netherlands

[21] Appl. No.: 367,908

[22] Filed: Jan. 3, 1995

Related U.S. Application Data

[63] Continuation of Ser. No. 688,790, Apr. 19, 1991, abandoned.

[30]   Foreign Application Priority Data

Apr. 20, 1990   [EP]   European Pat. Off. ............ 90.200989

[51] Int. Cl.$^6$ .................... A61K 39/102; A61K 39/00; A61K 39/02; C12N 1/00
[52] U.S. Cl. ................... 424/255.1; 424/236.1; 424/184.1; 435/243; 435/261; 530/350
[58] Field of Search ................ 424/246.1, 236.1, 424/255.1, 184.1, 823, 825; 530/412; 435/243, 261

[56]   References Cited

U.S. PATENT DOCUMENTS 5,047,237   9/1991   Cochran .................... 424/89

FOREIGN PATENT DOCUMENTS 0354628   2/1990   European Pat. Off. ..... A61K 39/102
8002113   10/1980   WIPO .

OTHER PUBLICATIONS

Fedorka–Cray et al. Inf & Imm 58:358–365 Feb. 1990.
Kamp et al. Journ. of Clinical Microb. 27: 1187–1191 1989.
Woodward et al. Journal of Immunological Methods 78:142–153 1985, Detection of Monoclonal Antibodies Specific for Carbohydrate Epitopes Using Periodate Oxidation.
Devenisk et al. Infect & Imm 1990: 3829–3832 vol. 58 (1).
Devenisk et al. Inf & Immun 57:3210–3213 Oct. 1989 (2).
Rycroft et al. Veterinary Microbiology 15: 303–314, 1987.
Rycroft et al Journal of General Microbiology Mar. 29, 1991 137: 561–568.
Mac Innes et al. Infect & Immunity 55: 1626–1634 1987.
J. I. MacInnes et al., "Analysis of Major Antigens of Haemophilus Pleuropneumoniae and Related Organisms", Biological Abstracts, vol. 84, 1987, Abstract No. 52672, Infection Immunology, vol. 55., No. 7, 1987, pp. 1626–1634.

*Primary Examiner*—Hazel F. Sidberry
*Attorney, Agent, or Firm*—Mary E. Gormley; William M. Blackstone

[57]   ABSTRACT

The present invention is concerned with vaccines effective in protecting pigs against porcine pleuropneumonia. Said vaccines comprising a hemolysin and/or macrophage toxin and a 42 kD OMP preparation derived from *Actinobacillus pleuropneumoniae* (App) cells induce a complete and heterologous protection against App infection.

9 Claims, 8 Drawing Sheets

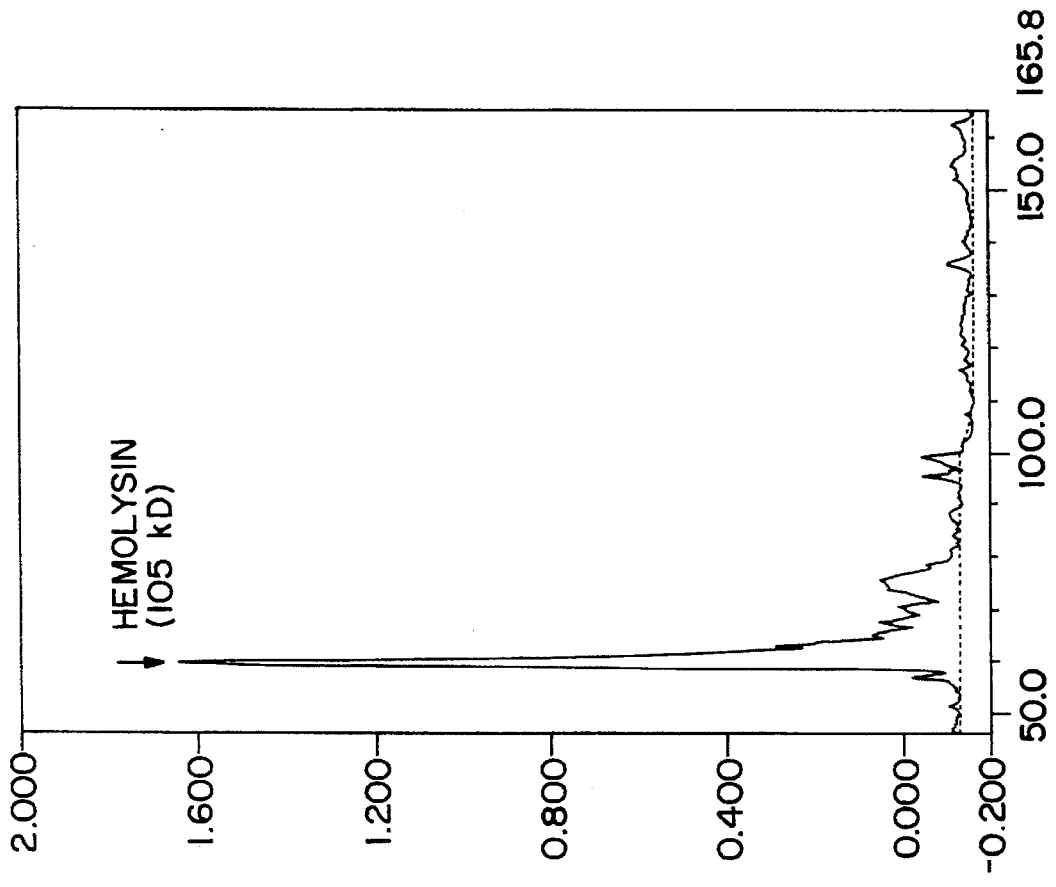
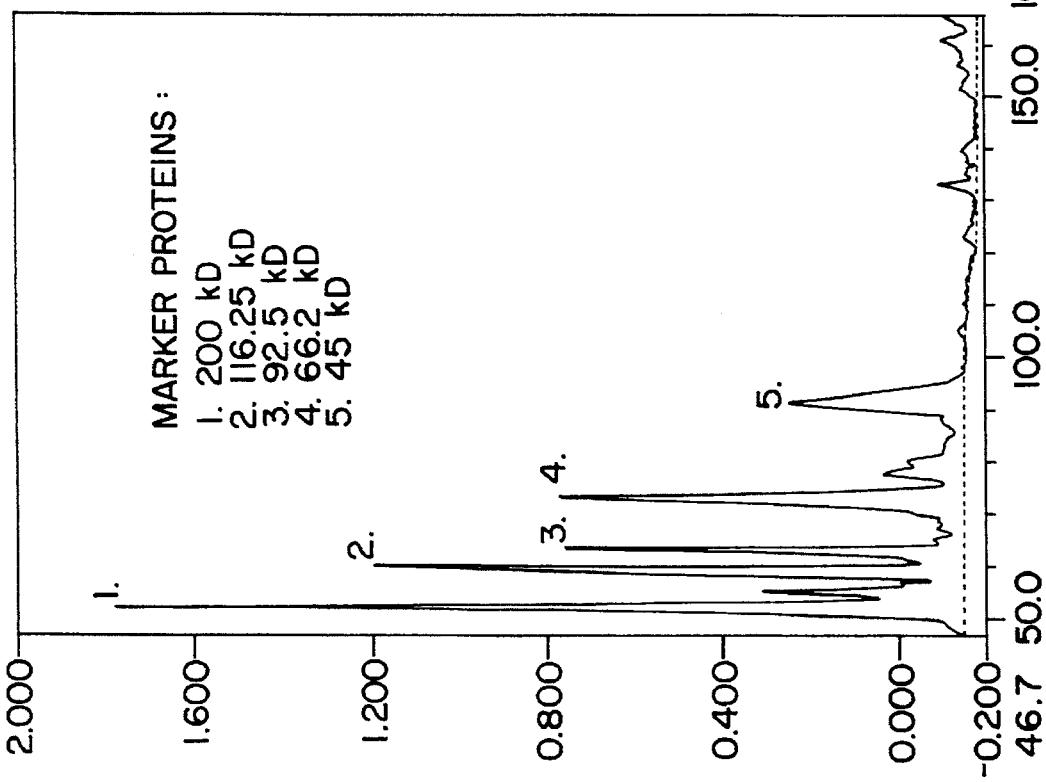

ACTINOBACILLUS PLEUROPNEUMONIAE SUBUNIT VACCINE

This is a continuation of application Ser. No. 07/688,790 filed Apr. 19, 1991, now abandoned.

BACKGROUND OF THE INVENTION

1) Field of the Invention

The invention is concerned with a vaccine composition for the protection of pigs against *Actinobacillus pleuropneumoniae* (App) infection and also with a method for protecting pigs by administering such a vaccine.

2) Description of the Prior Art

Porcine pleuropneumonia, a major respiratory disease in pigs, is spread out world-wide and causes severe economic losses to the pig industry due to peracute deaths, treatment of acutely sick pigs and the delays in marketing of chronically infected animals. As the etiological agent of this disease *Actinobacillus pleuropneumoniae* (*A. pleuropneumoniae*) has been identified. It is transmitted primarily by direct contact between animals, and the resulting infection produces a clinal course varying from peracute to chronic. The disease is primarily an infection of the respiratory tract having the clinical signs of high fever, severe respiratory distress, coughing and anorexia. The onset of the disease is rapid and morbidity and mortality are high. Pathologically of interest are the development and distribution of pneumonic lesions in the lungs.

Naturally, it has been attempted to control such *A. pleuropneumoniae* infections among pigs by vaccination programs.

To this end pigs have been vaccinated with bacterins, inactivated *A. pleuropneumoniae* bacteria. A disadvantage of such a vaccine is the concomitant serious side reactions. Furthermore, bacterin vaccination results primarily in antibodies elicited against (lipo)polysaccharides which are only specific for a certain serotype of *A. pleuropneumoniae* and hence are not protective against other *A. pleuropneumoniae* serotypes. In addition, bacterins of *A. pleuropneumoniae* only elicit a minor protection against field infection.

Capsule extracts of *A. pleuropneumoniae* have also been reported as protective antigens. However, immunization of pigs and mice with such extracts provided only partial immunity. In addition, capsule based vaccines only induce homologous protection, i.e. pigs vaccinated with a capsule vaccine derived from *A. pleuropneumoniae* of a specific serotype are not protected against challenge with *A. pleuropneumoniae* of a different serotype.

Live attenuated *A. pleuropneumoniae* vaccines also suffer from a number of drawbacks including the risk of inoculating animals with inadequately attenuated pathogens and the possibility that the attenuated bacteria may revert to a pathogenic state resulting in disease of the inoculated animals and the possible spread of the pathogens to other animals.

Hence, there is a long felt need for an *A. pleuropneumoniae* vaccine which is safe, serotype independent and induces a strong protective immune response in pigs.

SUMMARY OF THE INVENTION

It is therefore an object of the present invention to provide a subunit vaccine against porcine pleuropneumonia, essentially free from *A. pleuropneumoniae* cells, comprising substantially a combination of at least two different subunit components derived from *A. pleuropneumoniae*, said vaccine inducing good protection against *A. pleuropneumoniae* infection in pigs which in addition is serotype independent.

The present invention provides an *A. pleuropneumoniae* vaccine, essentially free from *A. pleuropneumoniae* cells, characterized in that the vaccine is derived from an outer-membrane protein preparation of *A. pleuropneumoniae* having a major dominant antigenic protein component of approximately 42 kD measured in SDS-PAGE, and at least one toxin selected from the group consisting of 1. a hemolysin (Hly) of *A. pleuropneumoniae* of approximately 105 kD in SDS-PAGE, and
2. a macrophage toxin (Mat) of *A. pleuropneumoniae* of approximately 120 kD in SDS-PAGE.

BRIEF DESCRIPTION OF THE DRAWINGS

FIGS. 4a and B Scan of SDS-PAGE gel ran with purified hemolysin (B) and marker proteins (A).

DETAILED DESCRIPTION OF THE INVENTION

Figure 1:
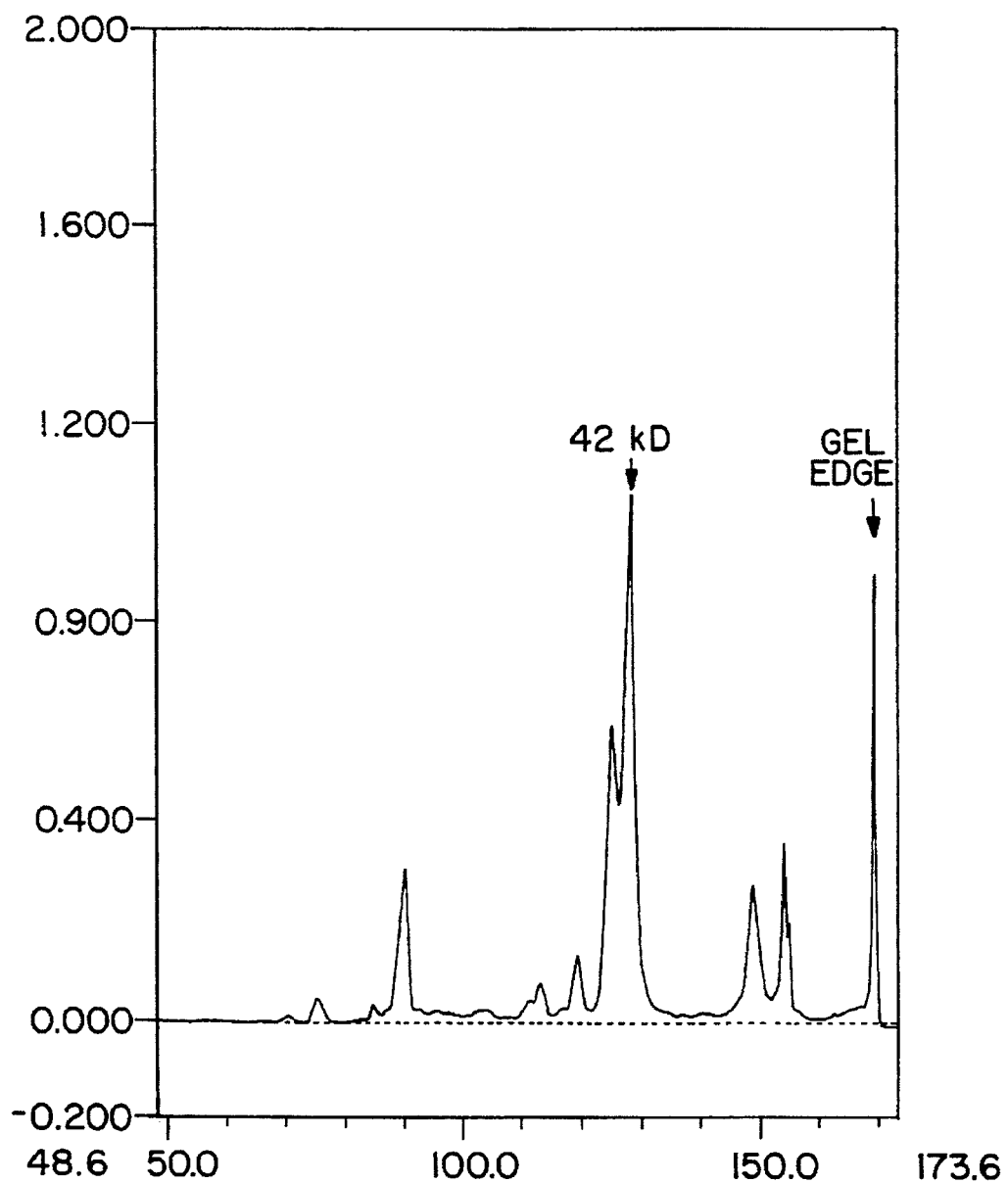
FIG. 1 Scan of SDS/PAGE gel ran with 42 kD enriched OMP preparation.

According to the present invention it has been found that the hemolysin and/or macrophage toxin of *A. pleuropneumoniae* combined with an outer membrane protein preparation of *A. pleuropneumoniae* having a major dominant antigenic protein component of about 42 kD measured in SDS-PAGE (further referred to as the 42 kD OMP preparation) can be applied as a vaccine against *A. pleuropneumoniae* infection in pigs, featuring outstanding protective properties not displayed by the prior art vaccines.

It is known that hemolysin induces some protection in pigs. However, vaccines comprising both a hemolysin and/or macrophage toxin, and a 42 kD OMP preparation induce complete and heterologous protection against challenge with virulent *A. pleuropneumoniae* bacteria (Example 3 and 5). The combination of the Hly or Mat component with the 42 kD OMP results in an increase of the protective properties of the vaccine which were unexpected.

Hemolysin (Hly) is characterized in that it
- is a calcium inducible protein, isolatable from an *A. pleuropneumoniae* cell culture supernatant
- has a molecular weight of 105±5 kD measured in SDS-PAGE (as outlined herein).
- dependent from the serotype from which hemolysin has been isolated, it has a hemolytic activity towards erythrocytes, which is
  sensitive to heat, and sensitive to proteinase K treatment.

The hemolytic activity of hemolysin can be established according the test outlined in Example 2.1.

The hemolytic activity of hemolysin is unstable and decays during storage in addition to the decrease of the molecular weight of the 105 kD protein which, however, does not result in the inactivation of the immunizing properties. Therefore, said hemolysins deprived of hemolytic activity or antigenic fragments of hemolysin which still have immunizing properties can also be incorporated into a vaccine according to the present invention.

Of serotypes 1–12 only types 1, 5a, 5b, 9, 10 and 11 produce a hemolysin with hemolytic activity (Example 2.1), the other serotypes producing equivalent non-hemolytic proteins of 105 kD which are serologically related to the 105 kD protein hemolysin with hemolytic properties (Example 2.3). Said immunological equivalents or fragments thereof are also referred to herein as hemolysins.

Furthermore, it is shown that antiserum elicited against hemolysin derived from one hemolytic serotype of A. pleuropneumoniae cross-neutralizes the hemolytic activity of the hemolysins derived from the other hemolytic A. pleuropneumoniae serotypes (Example 2.3).

In view of the above-mentioned close immunological relationship between hemolysins derived from different serotypes it is anticipated that a vaccine against A. pleuropneumoniae infection can be prepared which contains besides the 42 kD OMP preparation a hemolysin which can be derived from any of the available hemolytic A. pleuropneumoniae serotypes or strains.

A hemolysin to be incorporated into a vaccine according to the present invention can readily be obtained by culturing A. pleuropneumoniae cells under conditions promoting the expression of hemolysin and separating the supernatant from the cells. The hemolysin can be further purified by ultrafiltration and ammonium sulphate precipitation followed by molecular sieve chromatography.

During the purification process the fraction enriched in hemolysin derived from hemolytic strains can be monitored by its hemolytic activity towards erythrocytes according the test outlined in Example 2.1.

A member of the class of hemolysins to be incorporated into a vaccine according to the invention may be isolated from A. pleuropneumoniae cells of serotype 1 according to the procedure outlined below:

a. culturing said bacteria for 6 hours in Columbia broth supplemented with 0.01% NAD, 1% IsovitaleX and 25 mM $CaCl_2$;
b. concentrating the cell-free supernatant of the culture so obtained on a filter with a molecular weight cut-off value of 300,000 D;
c. precipitating from the concentrated supernatant by adding ammonium sulphate to 55% saturation and subsequent centrifuging the precipitate for 10 min. at 16,000×g;
d. separating the re-dissolved precipitate in 10 mM Tris-HCl buffer on a Sephacryl S-200 column;
e. collecting the first eluted peak.

This isolation procedure can also be applied to obtain hemolysins derived from other A. pleuropneumoniae serotypes (The purification and partial characterization of a serotype 1 hemolysin was also reported by Frey, J. and Nicolet, J., FEMS Microbiol. Letters (1988), 55, 41–46).

Macrophage toxin (Mat) is characterized in that it
is a protein obtainable from A. pleuropneumoniae cell culture supernatant,
has a molecular weight of 120±10 kD measured in SDS-PAGE (as outlined herein),
has an N-terminal amino acid sequence:

Ser(?)-Thr-Ile-Thr-Leu-Met, is cytotoxic for pig alveolar macrophages, which is
sensitive to heat, and
sensitive to proteinase K treatment.

The cytotoxic activity of Mat can be established according to the test outlined in Example 4.1.

The cytotoxic activity of Mat is unstable and decays during storage in addition to the decrease of the molecular weight of the 120 kD protein which, however is not essential for the immunizing properties of Mat.

Therefore, also said proteins deprived of their macrophage cytotoxic activity or antigenic fragments thereof which still have immunizing properties can also be incorporated into a vaccine according to the invention.

Of serotypes 1–12 A. pleuropneumoniae reference strains of serotypes 2, 3, 4, 6 and 8 produced Mat. Furthermore, it is demonstrated that antibodies elicited against Mat derived from cells of a specific serotype neutralizes the macrophage cytotoxic activity of the Mat preparation (Example 4).

In view of the close immunological relationship between Mat derived from different serotypes it is anticipated that a vaccine according to the invention can be prepared from any of the available A. pleuropneumoniae serotypes or strains producing Mat.

The Mat to be incorporated into a vaccine according to the present invention can readily be obtained by culturing A. pleuropneumoniae cells under conditions promoting expression of Mat and separating the supernatant from the cells. The Mat can be further purified by the steps of ultrafiltration, chromatography and concentration by ultrafiltration.

During the purification process the fraction enriched in Mat can be monitered by its macrophage cytotoxic activity according to the test outlined in Example 4.1.

A member of the macrophage cytotoxins to be incorporated into a vaccine according to the invention is characterized and obtainable by the following procedure:

a. culturing bacteria of A. pleuropneumoniae serotype 2 cells in Columbia broth supplemented with 0.01% NAD at 37° C. for about 6 hours;
b. concentrating the culture supernatant by ultrafiltration using a filter with a molecular weight cut-off value of 300.000 D;
c. eluting the concentrate over a CL4B column;
d. collecting the first eluted peak;
e. filtrating the toxin through a 0.45 µm cellulose acetate filter.

This isolation procedure can also be applied to obtain Mat from other strains of the same or different serotype.

The non-toxin component of a vaccine according to the present invention is an outer-membrane protein preparation of A. pleuropneumoniae cells which comprises a 42±5 kD protein measured in SDS-PAGE (as outlined herein) or an antigenic fragment thereof as a major dominant antigenic protein (42 kD OMP preparation), the 42 kD OMP being heat-modifiable
sensitive to proteinase K treatment.

Antiserum elicited against a 42 kD OMP preparation derived from serotype 1 cells strongly cross-reacts with cell lysates derived from serotypes 1–12 of A. pleuropneumoniae. As said antiserum mainly comprises antibodies recognising the 42 kD OMP in Western blotting it can be concluded that the 42 kD OMP is the major dominant antigenic protein in the purified OMP preparation (Example 1.2). From the above, it is anticipated that a vaccine against

*A. pleuropneumoniae* infection can be prepared which contains besides a hemolysin and/or Mat, a 42 kD OMP preparation which can be derived from any available *A. pleuropneumoniae* serotype.

Said 42 kD OMP preparation can be obtained by culturing *A. pleuropneumoniae* bacteria under conditions promoting the expression of the 42 kD OMP, sedimentation of the cell membrane fraction following disruption of *A. pleuropneumoniae* cells by e.g., sonication, grinding or french press, purifying said fraction further into inner and outer membranes e.g. by density gradient sedimentation or by differential solubilization of the inner membrane by detergents such as Triton X-100 or sarkosyl followed by centrifugation, and if desired preparing an OMP preparation further enriched in the 42 kD OMP.

A member of the class of outer-membrane protein preparations enriched in the 42 kD protein to be incorporated into a vaccine according to the invention, may be isolated from *A. pleuropneumoniae* cells of serotype 1 according to the procedure outlined below:

a. culturing said bacteria overnight in Brain Heart Infusion broth supplemented with 0.01% NAD;
b. harvesting bacterial cells by centrifugation and resuspending in 10 mM HEPES buffer;
c. disrupting bacterial cells by ultrasonic treatment;
d. removing of large cell debris by centrifugation and harvesting total membrane fragments from the supernatant by centrifugation for 1 hour at 100,000×g and resuspending in HEPES buffer;
e. adding of sodium N-lauroylsarcosinate (sarkosyl) to a final concentration of 1% (w/v) and stirring for 1 hour.
f. harvesting the outer membrane proteins by centrifugation at 100,000×g for 1 hour and resuspending in $H_2O$.

This isolation procedure can be applied to obtain 42 kD OMP preparations derived from all available *A. pleuropneumoniae* serotypes.

If desired, the 42 kD OMP can be purified to homogenity by methods known in the art, e.g. solubilizing the 42 kD OMP from said 42 kD OMP preparation by extraction with one or more detergents followed by further purification including ion exchange or molecular sieve chromatography, under conditions which do not affect the protective properties of the 42 kD OMP.

A hemolysin, Mat and a 42 kD OMP to be incorporated into a vaccine according to the invention can be obtained by chemical synthesis, purification from *A. pleuropneumoniae* cell culture or by recombinant DNA technology.

In the latter case nucleic acid sequences encoding abovementioned proteins or fragments thereof can for example be identified by screening a genomic *A. pleuropneumoniae* DNA bank for individual clones comprising said sequences, e.g. by using a specific reaction with polyclonal or monoclonal antibodies elicited against hemolysin, Mat or the 42 kD OMP. The nucleic acid sequences can be ligated to various expression effecting DNA sequences, resulting in a so called recombinant nucleic acid molecule which can be used for the transformation of a suitable host. Such hybrid DNA molecules can for example be derived from plasmids or from nucleic acid sequences present in viruses. The host cell can be of prokaryotic origin, e.g. bacteria or eukaryotic origin such as mammalian cells. The transformed host cells can be used to produce the hemolysin or 42 kD OMP whereafter said proteins can be isolated and subsequently incorporated into a vaccine according to the invention.

In another embodiment a live vector vaccine can be prepared comprising non-pathogenic micro-organisms, e.g. viruses or bacteria containing the genes encoding the hemolysin and/or Mat, and the 42 kD OMP cloned into the same or different micro-organisms.

A vaccine according to the present invention is derived from a hemolysin and/or Mat component, and a 42 kD OMP preparation component both being derived from *A. pleuropneumoniae*. The vaccine may comprise the respective components or antigenic fragments of said components which still have immunizing properties or may be in the form of a recombinant DNA vaccine as outlined above.

Suitable immunochemically active polypeptide fragments of protein components of the present vaccine containing (an) epitope(s) can be found by means of the method described in Patent Application WO 86/06487, Geysen, H. M. et al. (Proc. Natl. Acad. Sci. 81, 3998–4002, 1984), Geysen, H. M. et al. (J. Immunol. Meth. 102, 259–274, 1987) based on the so-called pepscan method, wherein a series of partially overlapping polypeptides corresponding with partial sequences of the complete polypeptide under consideration, are synthesized and their reactivity with antibodies is investigated.

In addition, a number of regions of the polypeptide, with the stated amino acid sequence, can be designated epitopes on the basis of theoretical considerations and structural agreement with epitopes which are now known. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

T-cell epitopes which may be necessary can likewise be derived on theoretical grounds with the aid of Berzofsky's amphiphilicity criterion (Science 235, 1059–62, 1987). Small fragments are preferably conjugated to carrier molecules in order to raise their immunogenicity. Suitable carriers for this purpose are macromolecules, such as natural polymers (proteins like key hole limpet hemocyanin, albumin, toxins), synthetic polymers like polyamino acids (polylysine, polyalanine), or micelles of amphiphilic compounds like saponins. Alternatively these fragments may be provided as polymers thereof, preferably linear polymers.

In particular, the hemolysin component is derived from *A. pleuropneumoniae* strains of serotype 1, 5a, 5b, 9, 10 or 11.

The Mat component in a vaccine according to the invention is preferably derived from *A. pleuropneumoniae* cells of serotype 2, 3, 4, 6 or 8.

The most preferred vaccine according to the invention is a trivalent vaccine derived from the 42 kD OMP preparation, the hemolysin and the Mat of *A. pleuropneumoniae*.

Very favourable results can be obtained with the trivalent vaccine if the 42 kD OMP is derived from serotype 1 cells, the hemolysin is derived from serotype 5b cells and the Mat is derived from serotype 2 cells.

The vaccine according to the invention can be administered in a conventional active immunization scheme: single or repeated administration in a manner compatible with the dosage formulation and in such amount as will be therapeutically effective and immunogenic. The administration of the vaccine can be done, e.g. intradermally, subcutaneously, intramuscalary, intravenously or intranasally.

On a per dose basis, the concentration of the components described above can range from about 1 μg to about 1 mg per pig. A preferable range is from about 25 μg to 200 μg per pig.

A vaccine according to the invention may be prepared by admixing the hemolysin and/or Mat component and 42 kD OMP preparation component to a composition with immunizing activity.

For parenteral administration, such as intramuscular injection, said components may be combined with a suitable pharmaceutically acceptable carrier, for example an aqueous medium or a water containing suspension, often mixed with other constituents, e.g. in order to increase the immunizing activity and/or shelf life. These constituents may be salts, PH buffers, stabilizers, emulsifiers, adjuvants to improve the immune response (oil-in-water emulsions e.g. of vitamin-E, water-in-oil emulsions, aluminium compounds, muramyl dipeptide, saponin, polyanions, amphipatic compounds or block (co)polymers) and preservatives.

The vaccine may also be combined with other immunizing components for other diseases to produce multivalent vaccines or with other medicaments, for example, antibiotics. For example, multivalent vaccines can be prepared comprising additionally antigenic material of one or more of the swine pathogens, e.g. pseudorabies virus, transmissible gastroenteritis virus, porcine parvovirus, swine influenza virus, *Mycoplasma hyopneumoniae, Escherichia coli, Erysipelothrix rhusiopathiae, Bordetella bronchiseptica* and *Pasteurella multocida*.

EXAMPLE 1

1. Purification and characterisation of 42 kD enriched outer membrane protein (OMP) preparation
Methods Purification of OMP's was carried out essentially as described by Barenkamp et al. (J. Infect. Dis. 143, 668–676; 1981).

App serotype 1 reference strain was cultured overnight in Brain Heart Infusion broth supplemented with 0.01% NAD, bacteria were harvested by centrifuging and resuspended in 10 mM Hepes buffer (pH 7.4). Bacterial cells were ultrasonically treated, while cooling in ice-water, with a Branson Sonifier (type B-12) until most bacteria were disrupted and the $OD_{660}$ had decreased by at least 90%. Large cell debris was removed by centrifuging at 5,000×g for 20 min., followed by centrifuging at 10,000×g for 10 min. Membranes were harvested from the supernatant by ultracentrifuging at 100,000×g for 1 hour, and resuspended in Hepes buffer. Large insoluble material was removed by centrifuging (11,000×g for 20 min.) and 5 µm filtration. Sodium N-lauroylsarcosinate (Sarkosyl) was added to the filtrate to a final concentration of 1% (w/v). After agitation for 1 hour, the Sarkosyl insoluble OMP's were pelleted at 100,000×g for 1 hour, resuspended in $H_2O$ and 0.45 µm filtrated.

Purified OMP preparations were run in SDS-PAGE by the method of Laemmli (Nature 227, 680–684; 1970).

The protein content was measured by a modified Folin-Ciocalteu assay (J. Biol. Chem. 773, 627; 1927) using BSA as standard, the carbohydrate content was measured by the phenol-sulphuric acid assay according to Dubois et al. (Anal. Chem. 28, 350–356; 1956) using glucose as standard.

Heat modifiability of OMP's was tested in SDS-PAGE by pretreatment of samples in sample buffer at various temperatures (30° C.–100° C.) for 10 min., before application to the gel.

Sensitivity of OMP's for Proteinase-K treatment was tested as follows. Samples were adjusted to approx. 0.05 mg/ml of protein in 10 mM Tris-HCl buffer (pH 7.5) supplemented with 5 mM EDTA and 0.5% SDS and containing 100 µg/ml of Proteinase-K (Boehringer). After incubation at 37° C. for 3 hours with gentle agitation and storage overnight at 4° C., Proteinase-K treated and sham treated samples were run in SDS-PAGE. Gels were stained with CBB or with silver (Wray et al., Anal. Biochem. 118, 197–203; 1981), or used for Western blotting with a convalescent pig serum (Anal. Biochem. 120, 46–51; 1982). Pig antisera used were all convalescent sera from pigs who had survived a field infection with App serotype 2 or 9, or from pigs who had survived experimental challenge with App serotype 1, 2, 5a or 9.
Results The protein-carbohydrate ratio of the purified OMP preparation was 1:0.8. SDS-PAGE with CBB staining of the purified OMP preparation revealed a 42 kD double band as the major protein, clearly enriched compared with total bacterial lysates and crude total membrane preparations. FIG. 1 shows an example of a gel scan of the purified OMP preparation, carried out with a Shimadzu Dual-Wavelength TLC Scanner (CS-930) connected with a Shimadzu Data Recorder (DR-2). The purity of the 42 kD protein appeared to be approx. 60% on protein basis.

Pretreatment of purified OMP's at various temperatures prior to SDS-PAGE revealed that after pretreatment at 70° C. or higher the 42 kD protein was the major band. After pretreatment below 60° C. the band at 42 kD was completely absent, whereas another major band at approx. 200 kD appeared. This 200 kD band was not present after pretreatment at 70° C. or higher. It was concluded that the 42 kD OMP is a heat-modifiable protein.

Figure 2:
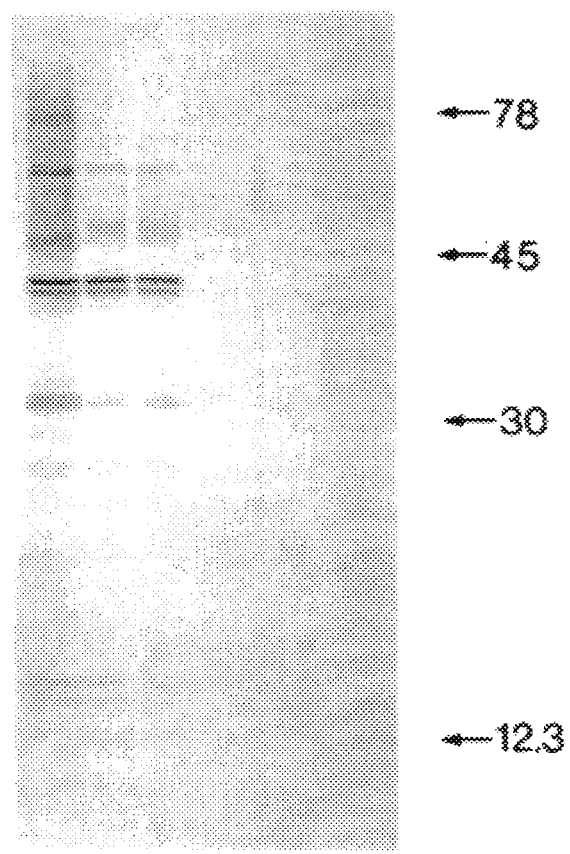
FIG. 2 Western blotting of Proteinase-K OMP preparations with convalescent pig serum. Lanes 1 and 4: crude OMP; lanes 2, 3, 5 and 6; purified OMP; lanes 1–3: sham treated; lanes 4–6: Proteinase-K treated.

Pretreatment of purified OMP's with Proteinase-K prior to SDS-PAGE and subsequent staining of gels with CBB showed that not any band was left after Proteinase-K treatment, also not the major 42 kD protein, whereas sham treatment had no effect on the protein pattern in the gels. Silver staining of the gels showed that only a very few low molecular weight bands (12–20 kD) were left after Proteinase-K treatment, whereas sham treated samples had the normal pattern of bands including the major 42 kD band. Western blotting of the gels with convalescent pig serum showed that not any band was developed after Proteinase-K treatment, whereas the normal pattern developed after sham treatment (FIG. 2). Apparently the convalescent pig serum did not contain antibodies directed against the Proteinase-K resistant low molecular weight bands seen in silver stained gels. It was concluded that the 42 kD OMP is sensitive to proteolytic action by Proteinase-K.

2. Antigenicity testing of purified 42 kD OMP
Methods

Guinea pigs were vaccinated subcutaneously with 20 µg purified 42 kD OMP, purified as described before, in a water-in-oil emulsion. Four weeks post-vaccination sera were collected and tested in Western blotting on bacterial lysates.

Figure 3:
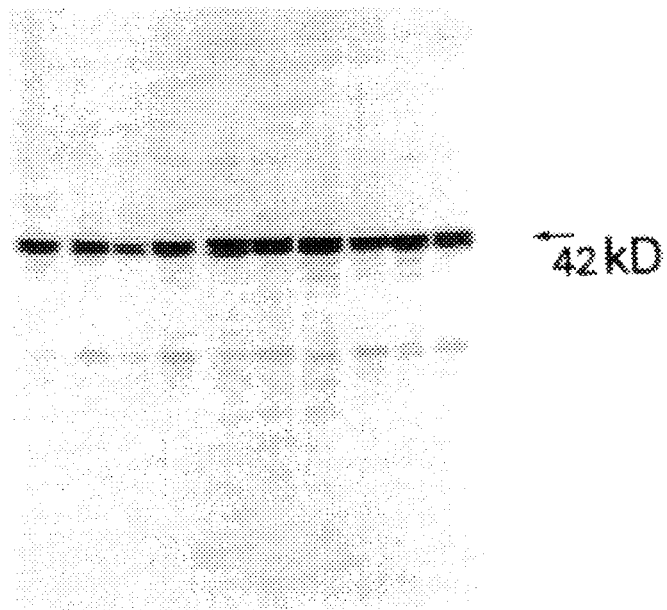
FIG. 3 Western blotting of bacterial lysates with post-vaccination serum.

(Bacterial lysates were prepared from App reference strains for serotypes 1–10 as follows. Bacteria were harvested from 3 large 15 cm chocolate agar plates per strain, suspended in approx. 10 ml PBS (0.04M, pH 7.2) with 0.3% formalin. Bacteria were lysed by ultrasonic treatment with a Branson Sonifier B-12, as long as necessary to get a reduction in the $OD_{660}$ of approx. 90%. Bacteria and large cell debris were spun down and the lysate was filtered through a 0.45 µm filter. The lysates were adjusted to a protein concentration of 1 mg/ml).
Results As shown in FIG. 3, the response on vaccination was mainly directed against the 42 kD (double) band. Although the vaccine was prepared from 42 kD OMP purified from App serotype 1 reference strain, antibodies recognised a similar 42 kD (double) band in lystes of App reference strains for serotypes 1 to 10. It was concluded that the 42 kD OMP is a common cross-reactive antigen, present in all App serotypes tested.

EXAMPLE 2

1. Hemolytic activity of App strains
Methods

Hemolytic activity of strains was tested essentially as described by Frey and Nicolet (Infec. Immun. 56, 2570–2575; 1988). Bacteria were grown in Columbia broth (Difco) supplemented with 1% IsoVitaleX™ (BBL), 0.01% β-NAD (Sigma) and 25 mM $CaCl_{12}$ (Merck) at 37° C. for 4–6 hours to mid-end log phase. Bacterial cells were spun down at 12,000×g for 10 min. and serial dilutions were made of the supernatant in Tris-buffered saline (TBS; 10 mM Tris-HCl in 0.85% NaCl, pH 7.5). Equal volumes of a 2% horse erythrocyte suspension in TBS were added to the supernatant dilutions. The mixtures were incubated at 37° C.

for 2 hours with agitation, followed by overnight static incubation at 4° C. for sedimentation of erytrocytes. The absorbance of the resulting supernatants was measured at 540 nm ($A_{540}$). In each assay at least four 100% controls were included, consisting of 1 part distilled water and 1 part 2% horse erytrocytes.

Negative controls consisted of 1 part TBS and 1 part erythrocytes. Hemolytic activity could be expressed as the dilution of the culture supernatant giving 25% hemolysis relative to the mean 100% control. Samples were considered positive when undiluted samples showed at least 25% hemolysis relative to the mean 100% control. Negative controls were used as a quality control for the erythrocyte suspension, not exceeding an A540 of 0.100.

Results

In Table 1 the results are shown for the App reference strains. Using the assay described in the Methods App serotypes 1, 5a, 5b, 9, 10 and 11 appeared to be hemolytic, whereas the other serotypes were negative. Testing App field isolates, in general the same serotypes were hemolytic.

TABLE 1

Hemolytic activity of A. pleuropneumoniae reference strains (in liquid culture)

| SEROTYPE | REFERENCE STRAIN NO. | HEMOLYTIC |
|---|---|---|
| 1 | 4074 | + |
| 2 | 1536 | – |
| 3 | 1421 | – |
| 4 | M62 | – |
| 5a | K17 | + |
| 5b | 120 | + |
| 6 | Femϕ | – |
| 7 | WF83 | – |
| 8 | 405 | – |
| 9 | 13261 | + |
| 10 | 13039 | + |
| 11 | 56153 | + |
| 12 | 8329 | – |

2. Purification and characterisation of hemolysin

Methods

For purification of hemolysin App serotype 1 or serotype 5b reference strain was grown in Columbia broth supplemented with 1% IsoVitaleX™, 0.01% NAD and 25 mM $CaCl_2$ at 37° C. for approx. 6 hours. All subsequent steps were performed at 4° C. Bacteria were removed by centrifuging (30 min. at 16,000×g) and 0.45 µm filtration using cellulose acetate membrane filters (Sartorius). The cell free supernatant was concentrated by ultrafiltration using the Minitan™ system (Millipore) with a PTMK filter (MW cut-off 300,000; polysulfone). Hemolysin was precipitated overnight in 55% saturated ammonium sulphate, centrifuged for 10 min. at 16,000×g and redissolved in 10 mM Tris-HCl buffer pH 7.5. Finally, the hemolysin was eluted over a Sephacryl S-200 or a CL4B column (Pharmacia) using 10 mM Tris-HCl buffer (pH 7.5) as elution buffer. The first eluted peak contained the hemolysin. Purified hemolysin preparations were run in SDS-PAGE by the method of Laemmli (Nature 227,680–684; 1970).

Crude hemolysin preparations were made from all serotypes by ammonium sulphate precipitation of culture supernatants. All preparations were stored at –70° C. unless otherwise stated.

Heat sensitivity was tested by heating culture supernatants for 10 min. at 60° C. and subsequent testing of hemolytic activity (see before). Sensitivity to proteinase-K treatment was tested by the incubation of culture supernatants with 0.02 mg/ml proteinase-K (Boehringer; from T. album) for 10 min. at 37° C. and subsequent testing of hemolytic activity. Sensitivity to trypsin was tested by the incubation of culture supernatant in the presence of 0.02 mg/ml trypsin (Sigma) for 10 min. at 37° C., followed by the addition of 0.03 mg/ml trypsin-inhibitor (Sigma) and another incubation for 10 min. at 37° C. Purified hemolysin, containing 0.6 mg/ml, was incubated with 0.1 mg/ml proteinase-K for 3 hours at 37° C. and subsequently subjected to SDS-PAGE. Stability of purified hemolysin was tested by storage of preparations at various temperatures for various periods and subsequent analysis in SDS-PAGE.

Results

Figure 5:
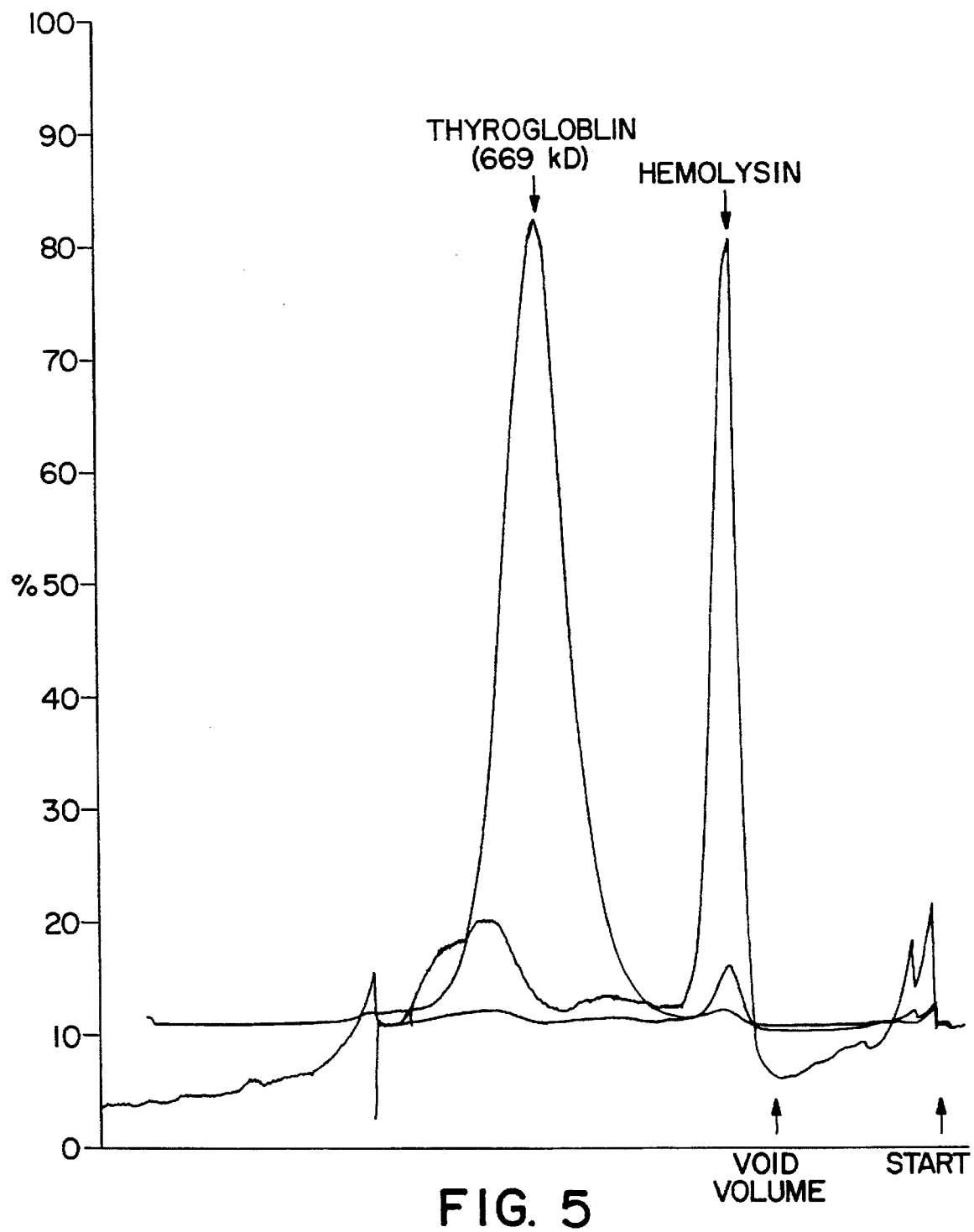
FIG. 5 Elution profile of hemolysin using a Sephacryl S-1000 column.

Hemolysin purified from serotype 1 and serotype 5b reference strain following the procedure described in the Methods, both showed a band in SDS-PAGE at 105 kD after CBB staining. A gel scan of purified serotype 5b hemolysin is shown in FIG. 4. Although the apparent MW in SDS-PAGE appeared to be approx. 105 kD, native hemolysin was retained during filtration using a filter with a MW cut-off of 300 kD. Furthermore, from the elution profile obtained in gel filtration it was concluded that the native hemolysin or aggregates thereof have a MW of at least $10 \times 10^6$ D (FIG. 5). Using a Sephacryl S-1000 (Pharamcia) column with bovine thyroglobulin (approx. MW 669 kD; Sigma) as marker protein, hemolysin was eluted just after the void volume whereas thyroglobulin was retained.

The protein-carbohydrate ratio of purified hemolysin preparations was approx. 10:1.

Crude hemolysin preparations from culture supernatant of the reference strains listed in Table 1, all showed a similar band at 105 kD in SDS-PAGE. So also the reference strains without hemolytic activity as tested by the described assay, all did show a 105 kD protein band similar to the hemolytic strains.

Purified hemolysin still had hemolytic activity, provided that the purification was performed within 2 to 3 days after cultivation of the bacteria. Hemolytic activity was stable when hemolysin was stored at –70° C., but was lost within a few days after storage at 4° C. or higher temperatures.

Figure 6:
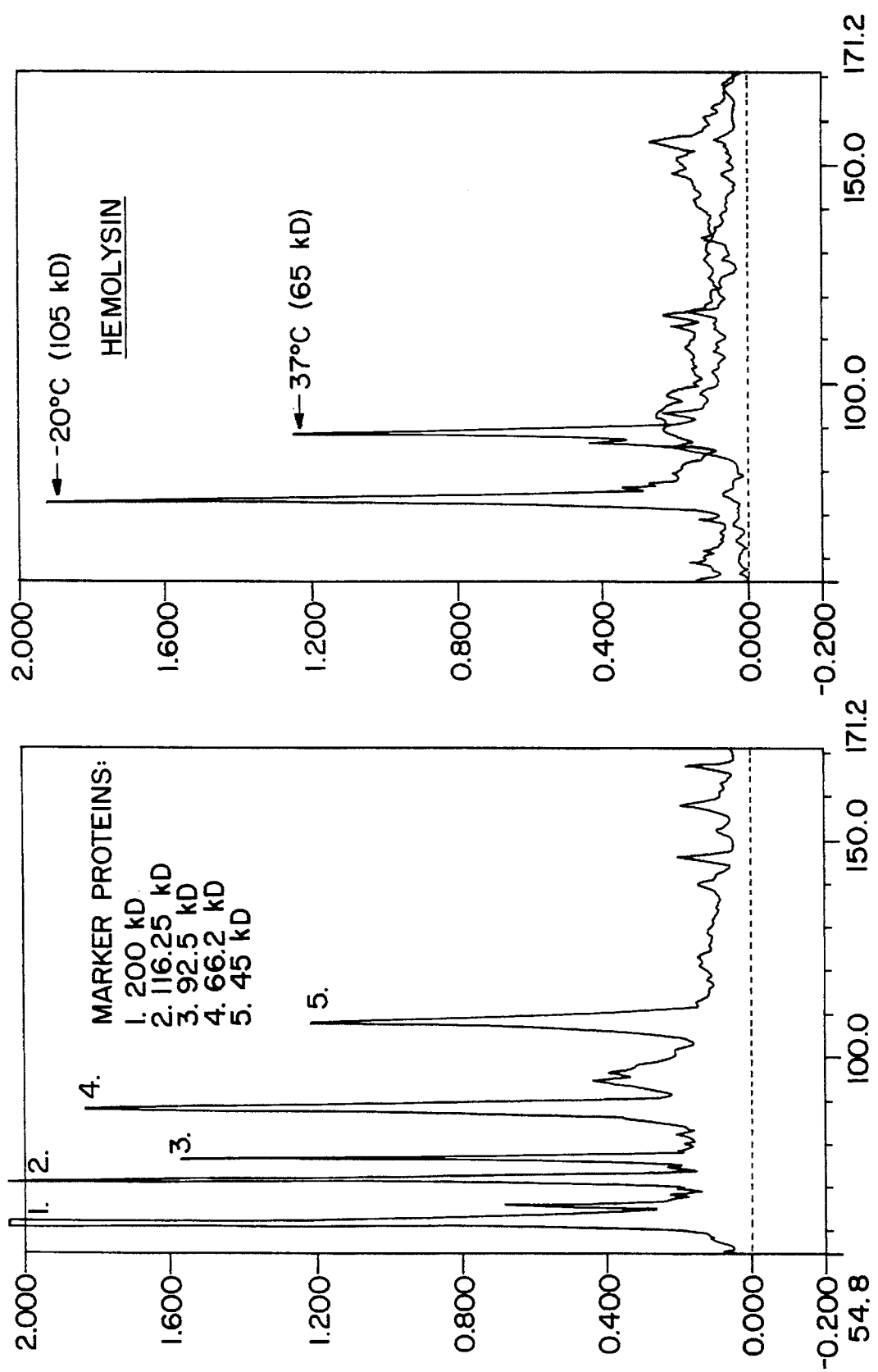
FIGS. 6a and B Gel scans of marker proteins (A) and purified hemolysin stored at −20° C. or at 37° C. (B).

Also in SDS-PAGE the 105 kD protein was not stable when purified hemolysin was stored at 4° C. or higher temperatures. Storage of hemolysin for 7 days at 4° C., room temperature or 37° C. caused a step-wise decrease in apparent MW of the protein band until approx. 65 kD after storage at 37° C. As an example FIG. 6 shows gel scans of purified hemolysin kept at –20° C. and at 37° C.

Hemolytic activity in culture supernatants of strains belonging to hemolytic serotypes (see Table 1) was abolished completely by heating for 10 min. at 60° C. Hemolytic activity of culture supernatants was also sensitive to proteinase-K or trypsin treatment. Addition of 0.5% formalin to cultures and incubation overnight at room temperature or at 37° C. also destroyed hemolytic activity.

3. Antigenicity testing of purified hemolysin and cross-reaction of antisera

Methods

Convalescent pig sera were collected from pigs who had survived an experimental infection with App serotypes 1, 2, 5a or 9, but had developed significant lung lesions typical for App infection.

Hyperimmune sera were raised in rabbits by two intramuscular injections with an interval of 6 weeks, with purified hemolysin, purified from serotype 1 or serotype 5b reference strains as described before. Rabbits were immunised with two doses of 100 µg purified serotype 1 hemolysin in Freund Complete and Freund Incomplete Adjuvant respectively. Rabbits were immunised with two doses of 25 µg purified serotype 5b hemolysin in tocol derivative emulsion. Hyperimmune sera were also raised in rabbits against hemolysin purified from App serotype 5b, stored for a prolonged period at various temperatures: –70° C., 4° C. and room temperature. Rabbits received 2 intramuscular doses of 25 µg hemolysin in a water-in-oil emulsion with a 6 weeks interval. The age of the preparations kept at various temperatures was 75 days at priming and 118 days at booster injection. All animals were of SPF quality or at least App-free as tested serologically (Elisa, Western blot) with the pre-immune sera. Antisera were collected at 2 weeks after the booster injection.

Monoclonal antibody (MAb) producing hybridoma lines were prepared by standard methods. Balb/c mice were immunised with purified hemolysin from App serotype 1, spleen cells were fused with Ag8 myeloma cells, and positive hybridoma cells were cloned by limiting dilution. MAb were harvested from hybridoma culture supernatant or from mouse ascitic fluid.

Elisa (Enzyme-linked immunosorbent assay) was performed by standard procedures, using purified serotype 1 and serotype 5b hemolysin as coating antigens. Antisera were prediluted 1:100 before making the serial dilutions. Background absorption values were calculated from 1:100 diluted pre-immune sera. Elisa titers were defined as the highest serum dilution giving an absorption value of at least 1.15 times the background absorption value.

Western blotting of crude hemolysin preparations and of purified hemolysin was performed as described before.

Neutralisation of hemolytic activity by antisera was tested as follows. Culture supernatants were prepared as described before. Antisera were prediluted 1:25 and serial dilutions were made in TBS. Equal volumes of undiluted culture supernatant were added to the antiserum dilutions, followed by incubation for 30 min. at 37° C. These mixtures were tested for hemolytic activity as described before. The neutralisation titer was defined as the serum dilution giving 50% hemolysis relative to the 2 times diluted culture supernatant. Pre-immune sera served as negative controls in each assay.

Results

As shown in Table 2, convalescent sera of pigs who survived infection with App serotype 1, 5a or 9 contained high antibody titers in Elisa against hemolysin purified from serotype 1 and 5b, and neutralised hemolytic activity of App serotype 1, 5b and 9 culture supernatants. Convalescent serotype 2 pig serum only contained moderate antibody titers in Elisa against serotypes 1 and 5b hemolysin whereas neutralisation of hemolytic activity could not be detected.

Hyperimmune rabbit antisera raised against purified hemolysin from App serotypes 1 and 5b both showed high antibody titers in Elisa against both serotype 1 and 5b hemolysin, and both antisera showed neutralisation of serotype 1, 5b and 9 hemolysin.

Figure 7:
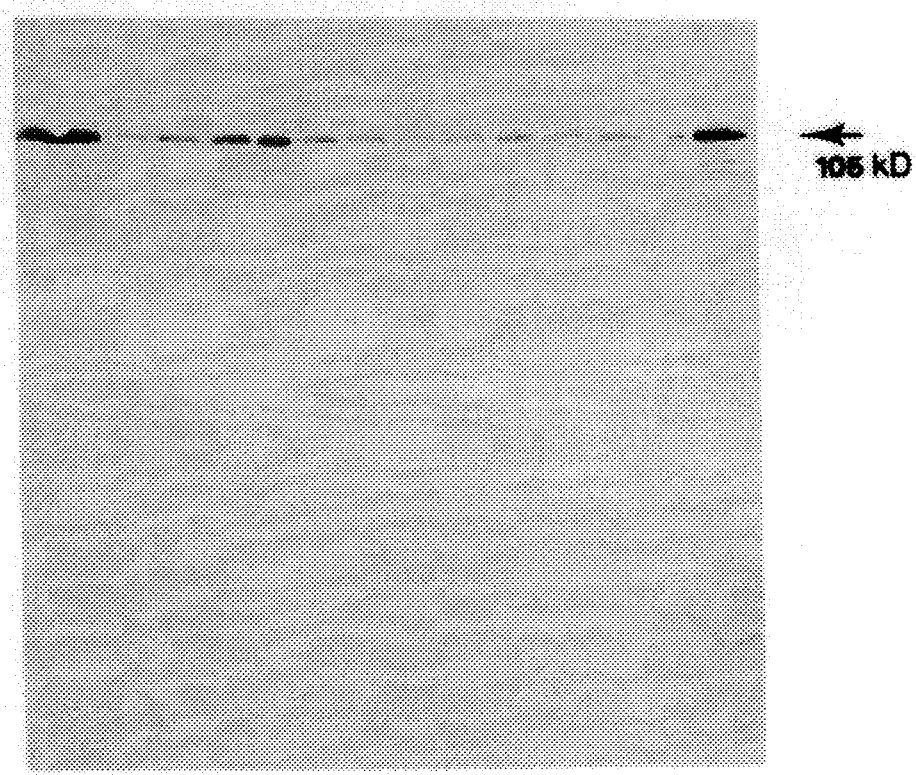
FIG. 7 Western blotting of crude hemolysin preparations and purified App serotypes 5b hemolysin (*) with monoclonal antibodies raised against App serotype 1 hemolysin.

Four different MAbs prepared against App serotype 1 hemolysin had high titers in Elisa against both serotype 1 and 5b hemolysin, but did not show any neutralisation of hemolytic activity. All App serotype 1 antisera tested (convalescent pig serum, hyperimmune rabbit serum and MAbs) reacted in Western blotting with the 105 kD band in purified serotype 1 and 5b hemolysin as well as with the 105 kD band in crude hemolysin preparations of all App serotypes (1–12). As an example, FIG. 7 shows the Western blot of crude hemolysin preparations and purified App serotype 5b hemolysin with one of the MAbs.

It was concluded 1) that the 105 kD labile hemolysin is antigenic both in active infection and after immunisation with purified hemolysin; 2) that the anti-hemolysin antibodies show cross-reaction with a similar 105 kD antigen produced by all App serotypes (1–12), including the strains without hemolytic activity as tested in the described assay; 3) that the provoked antibodies show cross-neutralisation of hemolytic activity of various serotypes, provided that the antibodies were induced by a 105 kD antigen from a hemolytic serotype. Obviously the MAbs recognise epitopes that are not involved in hemolytic activity.

As shown before, storage of purified hemolysin at temperature of 4° C. or higher resulted into a decrease of apparant MW in SDS-PAGE, step-wise from 105 kD to 65 kD. Antisera as listed in Table 2, raised against the 105 kD hemolysin, still reacted in Western blotting with aged hemolysin preparations with decreased apparent MW (data not shown). The antigenic properties of aged preparations after immunisation of rabbits are shown in Table 3. It was concluded that aged hemolysin with a decreased apparant MW in SDS-PAGE still gives rise to antibodies that are reactive with the original 105 kD hemolysin of App serotypes 1 and 5b. Some decrease in antibody titers could be observed, but also immunisation with the 65 kD aged hemolysin preparation yielded antisera with very high antibody titers. These antisera also showed neutralization of hemolytic activity.

TABLE 2

Cross-reactions of antisera with hemolysin preparations.

| Antiserum[a] | Elisa[b] | | Blot[c] | Neutralisation[d] | | |
|---|---|---|---|---|---|---|
| (serotype) | 1 | 5b | | 1 | 5b | 9 |
| CPS 168 (1) | ++ | ++ | + | + | + | + |
| CPS 261H (2) | + | + | nt | − | − | − |
| CPS 139 (5a) | ++ | ++ | nt | + | + | + |
| CPS 191 (9) | ++ | ++ | nt | + | + | + |
| HRS 3895 (1) | ++ | ++ | + | + | + | + |
| HRS 4609 (5b) | ++ | ++ | nt | + | + | + |
| MAbs (1) | ++ | ++ | + | − | − | − |
| PPS | − | − | − | − | − | − |
| PRS | − | − | − | − | − | − |

[a]CPS = convalescent sera from pigs infected with indicated App serotype.
HRS = hyperimmune rabbit sera against purified hemolysin from indicated App serotype.
Mabs = 4 different monoclonal antibodies, prepared against hemolysin from App serotype 1.
PPS and PRS = pre-immune pig and rabbit sera respectively.
[b]Antibody detection in Elisa against purified hemolysin from App serotypes 1 and 5b; − = titer < 100, + = 100 < titer < 1000, ++ = titer > 1000.
[c]Reaction with 105 kD band in crude hemolysin preparations of all App serotypes (1–12) and in purified hemolysin from App serotypes 1 and 5b; nt = not tested.
[d]Neutralisation of hemolytic activity in culture supernatant of App serotypes 1, 5b and 9.

TABLE 3

Antigenic properties of aged purified App serotype 5b hemolysin (means of 3 rabbit antisera for each preparation).

| Antigen | Prominant band(s) | Elisa[a] | |
|---|---|---|---|
| stored at | in SDS-PAGE at | 1 | 5b |
| −70° C. | 105 kD | 6.0 | 6.9 |
| 4° C. | 80 and 70 kD | 5.8 | 6.55 |
| roomtemp. | 65 kD | 5.4 | 6.2 |

[a]$^{10}$log titers in Elisa against purified 105 kD hemolysin from App serotypes 1 and 5b.

EXAMPLE 3

Protection of pigs against App challenge by vaccination
Methods

Challenge of pigs with App was carried out by aerosol exposure using a DeVilbiss 65 ultrasonic nebulizer (DeVilbiss Co., Pennsylvania, U.S.A). The use of this nebulizer has been recommended by Sebunya et al (Can. J. Comp. Med. 47, 48–53; 1983) for the study of App pathogenesis and more specifically for the evaluation of vaccines.

Challenges were carried out with App reference strains for serotypes 1 and 5a (Table 1). Bacteria were grown for approx. 6 hours in either Brain Heart Infusion broth supplemented with 0.01% NAD, or Columbia broth supplemented with 1% IsoVitaleX™ and 0.01% NAD, harvested by centrifugation and resuspended in saline to the desired concentration. Viable counts were carried out on chocolate agar plates.

Animals were housed under SPF conditions in controlled barrier rooms, after challenge under negative pressure.

For challenge approx. 50 ml of bacterial suspension was aerosolised during 15 min. The nebulizer was placed outside the challenge room and its aerosol chamber was connected through the wall with a perforated pipe at approx. 1.50 m above the floor. All vaccinated and control animals in one experiment were challenged together in the same challenge room. Animals were observed for 2 weeks after challenge. Deaths, as well as the surviving pigs at 2 weeks after challenge, were examined postmortem for pathological lesions. Typical App lung lesions, hemorrhagic necrotizing fibrinous pleuropneumonia, were scored on a scale of 0–4 on the basis of percentage of the lung affected: 0=no lesions; 1=<25% affected; 2=>25% but <50% affected; 3=>50% but <75% affected; 4=>75% affected.

Experiments were carried out with pigs of various origins, which were vaccinated at various ages with various vaccines and antigen doses, and challenged with App serotype 1 and 5a bacteria. All vaccines were administered intramuscularly in the neck in doses of 2 ml each. The time interval between first and second vaccination was 6 weeks, whereas pigs were challenged at 2 weeks after the second vaccination. Antigen doses included in the vaccines were calculated on the basis of total protein contents of purified preparations.

Antigens were 42 kD outer membrane protein (OMP) preparation purified as described in Example 1.1, hemolysin (Hly) purified as described in Example 2.2 or 2 commercially available vaccines containing inactivated App bacteria of various serotypes. These bacterins were administered according to the instructions of the manufacturers. Further details of each experiment are given in the Results.

Results

From experiment 1 (Table 4) it was concluded that both commercially available bacterins did not induce protection against challenge, although in both bacterins inactivated bacteria of the same serotype as the challenge strain (App1) were present.

In experiment 2 (Table 5) it was found that after vaccination of pigs with the combination of hemolysin and 42 kD OMP preparation, both purified from App serotype 1, almost complete protection against App 5a challenge was observed with regard to mortality as well as App lung lesions. The mean lung lesion score of 0.3 in this case means that one pig only had one small App lung nodule at dissection.

In experiment 3 (Table 6) very young pigs were vaccinated with various doses of the combination of hemolysin purified from App serotype 5b and 42 kD OMP preparation purified from serotype 1, and subsequently challenged with App serotype 1. Compared with control animals all pigs vaccinated with the various antigen doses were completely protected, both with regard to mortality from App infection and to App lung lesions.

Experiment 4 (Table 7) is very similar to experiment 3, with the origin and status of the pigs as the only difference. Where in experiment 3 SPF pigs were used without maternal antibodies against the vaccine antigens, in experiment 4 the pigs were born from sows with high antibody titers against the vaccine components. At the moment of vaccination at an age of 5 weeks the pigs had ELISA antibody titers between 1:100 and 1:1,000 against both vaccine components hemolysin and 42 kD OMP. Also in this experiment, using pigs with maternal antibodies, vaccination with the combination of hemolysin and 42 kD OMP preparation protected against challenge with App serotype 1.

From these vaccination experiments it was concluded that vaccination of pigs with both hemolysin and 42 kD OMP preparation together induced complete protection against App challenge. Protection was directed not only against the homologous App serotype (antigens purified from the same serotype as the App challenge serotype) but also against heterologous App serotypes (antigens purified from App serotypes different from the App challenge serotypes).

TABLE 4

Vaccination experiment No. 1[a)]

Vaccine[b)]

| Antigen (from sero-type) | Antigen dose (μg) | Challenge strain[c)] (serotype) | Mortality (deaths/ total) | Mean lung lesions[d)] |
|---|---|---|---|---|
| Delsuvac HP | (bacterin) | App1 | 1/3 | 2.0 |
| Pleurovac | (bacterin) | App1 | 2/3 | 3.3 |
| Control | — | App1 | 1/4 | 2.3 |

[a)]SPF pigs; first vaccination at an age of 12 weeks; 3 or 4 pigs per group
[b)]Delsuvac HP from Mycofarm, The Netherlands, containing App serotype 1,2,3,6,8 and 9 bacteria. Pleurovac from Bloxham Veterinary Products Ltd., Ireland, containing App serotype 1,2,3,4,6 and 8 bacteria.
[c)]Viable count challenge suspension: 1 × 10$^9$/ml.
[d)]App lung lesion score on a scale of 0–4 based on percentage of lung affected: 0 = no lesions, 1 = 1–25%, 2 = 26–50%, 3 = 51–75%, 4 = >75%.

TABLE 5

Vaccination experiment No. 2[a)]

Vaccine[b)]

| Antigen (from sero-type) | Antigen dose (μg) | Challenge strain[c)] (serotype) | Mortality (deaths/ total) | Mean lung lesions[d)] |
|---|---|---|---|---|
| Hly(1)/OMP(1) | 50/200 | App5a | 0/3 | 0.3 |
| control | — | App5a | 3/3 | 4.0 |

[a)]Commercial App-free pigs; first vaccination at an age of 8 weeks; 3 pigs per group
[b)]Vaccine formulation: water-in-oil emulsion
[c)]Viable count challenge suspension: 6 × 10$^6$/ml
[d)]See legend Table 4.

TABLE 6

Vaccination experiment No. 3[a)]

Vaccine[b)]

| Antigen (from sero-type) | Antigen dose (μg) | Challenge strain[c)] (serotype) | Mortality (deaths/ total) | Mean lung lesions[d)] |
|---|---|---|---|---|
| Hly(5b)/OMP(1) | 50/200 | App1 | 0/3 | 0 |
| Hly(5b)/OMP(1) | 50/50 | App1 | 1/3[e] | 0 |
| Hly(5b)/OMP(1) | 12.5/50 | App1 | 1/3[e] | 0 |
| control | — | App1 | 2/3 | 3.0 |

[a)]SPF pigs; first vaccination at an age of 4 weeks; 3 pigs per group
[b)]Vaccine formulation: tocol derivative emulsion
[c)]Viable count challenge suspension: 7.4 × 10$^8$/ml
[d)]See legend Table 4
[e)]In the indicated groups one animal died by unknown reason, without any typical App signs or pathology.

TABLE 7

Vaccination experiment No. 4[a]

| Vaccine[b] | | | | |
|---|---|---|---|---|
| Antigen (from sero-type) | Antigen dose (μg) | Challenge strain[c] (serotype) | Mortality (deaths/total) | Mean lung lesions[d] |
| Hly(5b)/OMP(1) | 50/200 | App1 | 0/3 | 0 |
| Hly(5b)/OMP(1) | 50/50 | App1 | 0/3 | 0.3 |
| Hly(5b)/OMP(1) | 12.5/50 | App1 | 0/3 | 0.7 |
| control | — | App1 | 1/3 | 3.0 |

[a] Commercial pigs with maternal antibodies; first vaccination at an age of 5 weeks; 3 pigs per group
[b] Vaccine formulation: tocol derivative emulsion
[c] Viable count challenge suspension: $7.4 \times 10^{8/ml}$
[d] See legend Table 4

EXAMPLE 4

1. Cytotoxic activity of App strains

Methods

For cytotoxicity testing App culture supernatants were incubated with pig alveolar macrophages. Alveolar macrophages were isolated by flushing pig lungs with Hank's Balanced Salt Solution (Flow) supplemented with 0.01M EDTA and 20 mM Hepes, pH 7.4. Cells were washed 3 times in the same solution without EDTA, and after the last centrifugation cells were suspended in RPMI 1640 medium (Flow) supplemented with 10% Fetal Calf Serum (Gibco) and finally adjusted to a concentration of $2\times10^6/ml$. Tissue culture plates (24 wells; Costar) with circular glass coverslips (φ12 mm; Tamson) in each well were seeded with 0.5 ml per well of the final cell suspension, and macrophages were allowed to attach for 2 hours at 37° C. in a 5% $CO_2$ atmosphere. Subsequently the plates were washed 3 times with RPMI 1640 without serum.

Bacteria were grown in Columbia broth (Difco) supplemented with 0.01% β-NAD (Sigma) at 37° C. for 4–6 hours to mid-end log phase. Bacteria were removed by centrifugation and 0.5 ml of supernatant was added per well to the tissue culture plate with macrophages. After 2 hours incubation at 37° C. the coverslips with macrophages were washed 3 times with RPMI 1640 and placed upside down on glass slides on a drop of 20 μl of 0.05% Trypan Blue (Merck) in PBS. The percentage of dead cells, stained blue by taking up the Trypan Blue, was determined by phase-contrast microscopy. Negative controls consisted of macrophages incubated with Columbia broth.

Results

As shown in Table 8, all App reference strains were cytotoxic for alveolar macrophages, an activity that was secreted by the bacteria. Negative controls showed 10% or less toxicity for macrophages.

Whereas cytotoxicity of hemolytic strains can be accountable to the hemolysin described in Example 2, the non-hemolytic strains should produce other toxic molecules. In contrast to hemolytic activity, macrophage toxicity was also expressed when bacteria were grown in the absence of supplemented $CaCl_2$.

TABLE 8

Toxicity for pig alveolar macrophages, hemolytic activity, and SDS-PAGE of App reference strain culture supernatants

| Serotype (reference strain) | Toxicity for macrophages[a] | Hemolytic[b] | Presence in SDS-PAGE | |
|---|---|---|---|---|
| | | | 105 kD | 120 kD |
| 1 | 75 | + | + | − |
| 2 | 100 | − | + | + |
| 3 | 100 | − | + | + |
| 4 | 85 | − | + | + |
| 5a | 90 | + | + | − |
| 5b | 90 | + | + | − |
| 6 | 90 | − | + | + |
| 7 | 80 | − | + | − |
| 8 | 75 | − | + | + |
| 9 | 70 | + | + | − |
| 10 | 65 | + | + | ±[c] |
| 11 | 85 | + | + | − |
| 12 | 55 | − | + | − |
| Broth | 10 | − | − | − |

[a] Percentage dead macrophages determined as described in Methods of this Example.
[b] Hemolytic as determined in the assay described in Example 2.1.
[c] A visible band somewhat higher than at 120 kD position, and not reactive with monoclonal antibody Int 33-8 (see Example 4.3).

2. Purification and characterisation of App macrophaqe toxin (Mat)

Methods

For purification of the macrophage toxic activity App serotype 2, a nonhemolytic strain according to Example 2, was grown in Columbia broth supplemented with 0.01% NAD at 37° C. for approx. 6 hours. Further purification was performed essentially as described in Example 2.2 for hemolysin purification, including removing of bacteria by centrifugation, concentrating the culture supernatant by ultrafiltration using a filter with a MW cut-off of 300,000, and eluting the concentrate over a Sepharose CL4B column. The first eluted peak contained the toxic activity. The toxin could be filtrated through a 0.45 μm cellulose acetate filter (Sartorius) without loss of activity or antigen.

Crude Mat preparations were made from all serotypes by ammonium sulphate precipitation of culture supernatants. All preparations were stored at −70° C. or −20° C. unless otherwise stated.

Heat sensitivity, proteinase-K sensitivity, and stability of Mat was tested as described in Example 2.2 for hemolysin. SDS-PAGE was carried out by the method of Laemmli.

N-terminal amino acid analysis was performed on a sample obtained after applying the Mat preparation prepared as described above to electrophoresis and electroblotting.

Briefly, PAGE gels were prepared with a running gel buffer used in the Laemmli system (Nature 227, supra). After the electrophoresis proteins are blotted on PVDF (Immobilon-p®, Water/Millipore) using 10 mM CAPS pH 9–11/10% methanol as transfer buffer.

Protein from the blot is used for sequence analyses performed by Edman degradation with an automated sequenator (pulse-liquid, Model 477A, Applied Biosystems) on-line connected to an HPLC (Model 120A, Applied Biosystems) for identification of the step-wise release of PTH-amino acids.

Results

Macrophage toxin (Mat) purified from serotype 2 reference strain by the procedure described above, still showed toxic activity provided that purification was performed within 2 to 3 days at 4° C. Since the serotype 2 reference strain produces an inactive hemolysin as described in Example 2, the 120 kD band is considered to represent the Mat.

Evaluation of crude Mat preparations showed a similar 120 kD band in SDS-PAGE in supernatants of serotypes 2, 3, 4, 6 and 8. Serotype 10 culture supernatant showed a band at a position somewhat higher than 120 kD (Table 8). A similar 120 kD band was also seen in a number of serotype 2 and 5 field isolates.

Macrophage toxicity was abolished completely after treatment of Mat preparations at temperatures of at least 60° C. for 15 min., or after treatment with proteinase-K. The 120 kD protein in SDS-PAGE was stable at storage at −20° C., but 3 months storage at 4° C. resulted into desintegration of the 120 kD band in SDS-PAGE.

The N-terminal amino acid sequence analysis of Mat revealed the following amino acid sequence:

Ser(?)-Thr-Ile-Thr-Leu-Met (?) means a tentative assignment of the amino acid.

3. Antigenicity of macrophage toxin (Mat) and cross-reaction of antisera

Methods

Convalescent pig sera as described in Example 2.3. were used. Monoclonal antibody (MAb) producing hybridoma cell lines were prepared by standard methods; in screening hybridomas were selected producing MAb that were reactive with purified Mat from App serotype 2 but not reactive with purified App serotype 1 or 5b hemolysin in Elisa.

Western blotting was performed as described before. Neutralisation of Mat activity was tested by adding equal volumes of App culture supernatant to antiserum dilutions, followed by incubation for 30 min. at 37° C., prior to toxicity testing as described in Example 4.1.

Results

Convalescent sera of pigs who survived infection with App serotype 2, but not sera of pigs infected with App serotypes 1, 5a and 9, recognized the 120 kD band of Mat preparations in Western blotting. Convalescent App serotype 2 sera also neutralized Mat activity.

Figure 8:
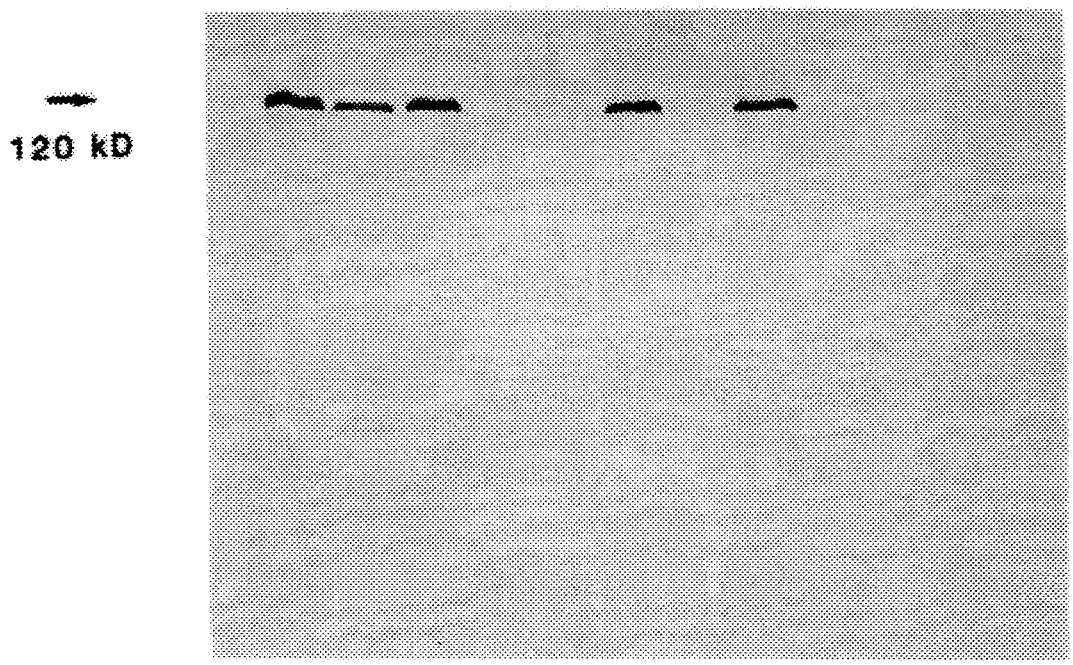
FIG. 8 Western blotting of crude Mat preparations with monoclonal antibodies raised against Mat or App serotype 2.

MAb Int 33-8 neutralized Mat activity and cross-reacted in Western blotting with a 120 kD band in crude Mat preparations of serotypes 2, 3, 4, 6 and 8 but not of other (reference) serotypes (FIG. 8).

A reaction with a 120 kD band was also seen in crude Mat preparations of serotype 2 field isolates and of some serotype 5 field isolates. MAb Int 33-4 reacted in Western blotting only with the 120 kD band of serotype 2 preparations and not with preparations from other serotypes.

As described before, storage of purified Mat at 4° C. for 3 months resulted into desintegration of the 120 kD band as seen in SDS-PAGE stained with CBB. However, Western blotting of such aged preparations showed bands at approx. 70–80 kD reactive with MAb Int 33-8.

EXAMPLE 5

Protection of pigs against App challenge by vaccination with a trivalent vaccine Methods Challenge was carried out as described in Example 3. In one experiment (no. 8) pigs were challenged intranasally with 1 ml of a 6 h culture containing $10^6$ viable bacteria. Challenge strains used were App serotype 1 reference strain, or App field isolates with serotype 2 or 9.

Vaccination was carried out as described in Example 3. Antigen doses included in the vaccines were calculated on the basis of total protein contents of purified preparations. Antigens were 42 kD outer membrane protein (OMP) purified as described in Example 1.1, 105 kD hemolysin (Hly) purified as described in Example 2.2, and 120 kD macrophage toxin (Mat) purified as described in Example 4.2.

Further details of each experiment are given in the results.

Results

In experiment 5 (Table 9) the bivalent 105 kD hemolysin and 42 kD OMP vaccine, also used in Example 3, was tested for protection against an App serotype 2 challenge. As shown, the vaccine did induce some protection against lesions but did not protect completely against serotype 2 challenge. So it was concluded that the vaccine has to contain an extra component, e.g. the 120 kD macrophage toxin described in Example 4, in order to be also completely protective against App serotype 2.

In experiment 6 (Table 10) pigs were vaccinated with either a vaccine containing 120 kD macrophage toxin (Mat) purified from serotype 2 and 42 kD OMP purified from serotype 1, or a vaccine containing 120 kD Mat purified from serotype 2, 42 kD OMP purified from serotype 1, and 105 kD hemolysin (Hly) purified from serotype 5b. It was found that the bivalent vaccine containing 120 kD Mat and 42 kD OMP did not protect against lesions after challenge with App serotype 1. This lack of protection was expected since according to Example 3 the vaccine has to contain 105 kD hemolysin in order to protect against App serotype 1, and the App serotype 1 strain used for challenge did not express 120 kD Mat.

Surprisingly the addition of 105 kD Hly purified from serotype 5b cells to the bivalent vaccine induced full protection against App serotype 1 challenge.

In experiment 7 (Table 11) the same bivalent and trivalent vaccines as in experiment 6 were tested for protection against App serotype 2 challenge. As shown, both vaccines protected very well against App serotype 2 challenge, both with regard to mortality and lung lesions. So addition of the 120 kD Mat to the bivalent 105 kD Hly/42 kD OMP vaccine makes the vaccine also protective against App serotype 2.

In experiment 8 (Table 12) it was found that the same trivalent vaccine as used in experiment 7, containing 120 kD Mat, 42 kD OMP and 105 kD Hly, also protected pigs against a completely heterologous challenge with an App serotype 9 strain.

TABLE 9

Vaccination experiment No. 5[a)]

| Vaccine[b)] | | | | |
|---|---|---|---|---|
| Antigen (from serotype) | Antigen dose (μg) | Challenge strain[c)] (serotype) | Mortality (deaths/ total) | Mean lung lesions[d)] |
| Hly(5b)/OMP(1) | 50/200 | HV 109 (2) | 0/3 | 1.7 |
| control | — | HV 109 (2) | 0/3 | 2.0 |

[a)]SPF pigs; first vaccination at an age of 12 weeks; 3 pigs per group
[b)]Vaccine formulation: tocol derivative emulsion
[c)]Viable count challenge suspension: $1.9 \times 10^8$/ml
[d)]See legend Table 4.

TABLE 10

Vaccination experiment No. 6[a]

Vaccine[b]

| Antigen (from sero-type) | Antigen dose (μg) | Challenge strain[c] (serotype) | Mortality (deaths/total) | Mean lung lesions[d] |
|---|---|---|---|---|
| Mat(2)/OMP(1) | 50/200 | App1 | 0/3 | 1.7 |
| Mat(2)/OMP(1)/Hly(5b) | 50/200/50 | App1 | 0/3 | 0.0 |
| control | — | App1 | 0/3 | 1.5 |

[a]SPF pigs; first vaccination at an age of 7 weeks; 3 pigs per group
[b]Vaccine formulation: tocol derivative emulsion
[c]Viable count challenge suspension: 2.1 × 10$^9$
[d]See legend Table 4.

TABLE 11

Vaccination experiment No. 7[a]

Vaccine[b]

| Antigen (from sero-type) | Antigen dose (μg) | Challenge strain[c] (serotype) | Mortality (deaths/total) | Mean lung lesions[d] |
|---|---|---|---|---|
| Mat(2)/OMP(1) | 65/50 | HV 111 (2) | 0/2* | 0.0 |
| Mat(2)/OMP(1)/Hly(5b) | 65/50/50 | HV 111 (2) | 0/3 | 0.3 |
| control | — | HV 111 (2) | 2/3 | 3.3 |

[a]SPF pigs; first vaccination at an age of 12 weeks; 3 pigs per group except * where 1 pig died before challenge
[b]Vaccine formulation: tocol derivative emulsion
[c]Viable count challenge suspension: 5 × 10$^8$/ml
[d]See legend Table 4.

TABLE 12

Vaccination experiment No. 8[a]

Vaccine[b]

| Antigen (from sero-type) | Antigen dose (μg) | Challenge strain[c] (serotype) | Mortality (deaths/total) | Mean lung lesions[d] |
|---|---|---|---|---|
| Mat(2)/OMP(1)/Hly(5b) | 65/50/50 | 4915 (9) | 0/8 | 0.3 |
| control | — | 4915 (9) | 2/8 | 2.3 |

[a]SPF pigs; first vaccination at an age of 5 weeks; 8 pigs per group
[b]vaccine formulation: tocol derivative emulsion
[c]Intranasal challenge with 10 viable bacteria
[d]See legend Table 4.

I claim:

1. A parenteral vaccine composition for the protection of pigs against Actinobacillus pleuropneumoniae infection, which is essentially free from A. pleuropneumoniae cells, comprising an outer-membrane protein preparation of A. pleuropneumoniae having a major dominant antigenic protein component of approximately 42 kD measured in SDS-PAGE, and at least one toxin selected from the group consisting of a hemolysin of A. pleuropneumoniae of approximately 105 kD in SDS-PAGE, and a macrophage toxin of A. pleuropneumoniae of approximately 120 kD in SDS-PAGE and an adjuvant.

2. Vaccine according to claim 1, comprising the outer-membrane protein preparation, hemolysin and macrophage toxin.

3. Vaccine according to claim 1, comprising at least one hemolysin selected from the group consisting of the hemolysins of serotypes 1, 5a, 5b, 9, 10 and 11 cells.

4. Vaccine according to claim 1, comprising at least one macrophage toxin selected from the group consisting of the macrophage toxins of serotypes 2, 3, 4, 6 and 8 cells.

5. Vaccine according to claim 2, derived from the outer-membrane protein preparation of serotype 1 cells, the hemolysin of serotype 5b cells and the macrophage toxin of serotype 2 cells.

6. Vaccine according to claim 1, further comprising antigenic material from at least one other porcine pathogen.

7. Vaccine according to claim 6, comprising pseudorabies virus or swine influenza virus.

8. Process for protecting pigs against A. pleuropneumoniae infection, comprising parenterally administering an immunizing amount of vaccine according to claim 1 to a pig.

9. Process for the preparation of a vaccine for the protection of pigs against Actinobacillus pleuropneumoniae infection, essentially free from A. pleuropneumoniae cells, containing A. pleuropneumoniae antigenic material derived from an outer-membrane protein preparation of A. pleuropneumoniae having a major dominant antigenic protein component of approximately 42 kD meausred in SDS-PAGE, comprising culturing bacteria of A. pleuropneumoniae under conditions promoting expression of a 42 kD outer-membrane protein, disrupting A. pleuropneumoniae cells, and mixing with at least one toxin selected from the group consisting of a hemolysin of A. pleuropneumoniae of approximately 105 kD in SDS-PAGE, and a macrophage toxin of A. pleuropneumoniae of approximately 120 kD in SDS-PAGE.

* * * * *